(12) United States Patent
Ruenitz

(10) Patent No.: US 6,323,190 B1
(45) Date of Patent: Nov. 27, 2001

(54) ESTROGEN MIMETICS LACKING REPRODUCTIVE TRACT EFFECTS

(75) Inventor: Peter C. Ruenitz, Athens, GA (US)

(73) Assignee: The Univeristy of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 09/363,911

(22) Filed: Jul. 28, 1999

Related U.S. Application Data
(60) Provisional application No. 60/094,944, filed on Jul. 31, 1998.

(51) Int. Cl.[7] ............... A61K 31/66; A61K 31/19; C07D 257/06; C07C 59/48

(52) U.S. Cl. ............... 514/129; 514/130; 514/381; 514/568; 514/569; 548/250; 548/252; 562/21; 562/468; 562/491

(58) Field of Search ............... 514/129, 130, 514/381, 568, 569; 548/252, 250; 562/21, 468, 491

(56) References Cited

U.S. PATENT DOCUMENTS

| | | | |
|---|---|---|---|
| 2,914,563 | 11/1959 | Allen et al. | 260/570 |
| 3,883,513 | * 5/1975 | Hess et al. | 260/240 |
| 4,522,811 | 6/1985 | Eppstein et al. | 514/2 |
| 4,894,373 | 1/1990 | Young | 514/239.2 |
| 4,938,949 | 7/1990 | Borch et al. | 424/10 |
| 5,189,212 | 2/1993 | Ruenitz | 562/468 |
| 5,428,181 | * 6/1995 | Sugioka et al. | 552/506 |
| 5,466,815 | * 11/1995 | Enhsen et al. | 548/252 |

OTHER PUBLICATIONS

Fujisaki, J. et al "osteotropic drug delivery system based on bisphosphonic prodrug . . . " Biol. Pharm. Bull. vol. 20 No. 11 pp. 1183–1187, 1997.*

Bignon et al., "Effect of Triphenylacrylonitrile Derivatives on Estradiol–Receptor Binding and on Human Breast Cancer Cell Growth," *J. Med. Chem.*, 32:2092–2103 (1989).

Brandes et al., "Correlation of the Antiproliferative Action of Diphenylmethane–Derivative Antiestrogen Binding Site Ligands with Antagonism of Histamine Binding but not of Protein Kinase C–mediated Phosphorylation," *Cancer. Res.*, 48:3954–3958 (1988).

Carini et al., "Nonpeptide Angiotensin II Receptor Antagonists: The Discovery of A Series of N–(Biphenylylmethyl)imidazoles as Potent, Orally Active Antihypertensives," *J. Med Chem.*, 34:2525–2547 (1991).

Emmens, "Halogen–Substituted Oestrogens Related to Triphenylethylene," *J. Endocrinol.*, Dodds, E.C.; Williams, P.C.; eds., 5:170–173 (1946–48).

Francis et al., "The Development of Diphosphonates as Significant Health Care Products," *J. Chem. Educ.* 55(12):760–766 (1978).

Frolik et al., "Time–Dependent Changes in Biochemical Bone Markers and Serum Cholesterol in Ovariectomized Rats: Effects of Raloxifene HCl, Tamoxifen, Estrogen, and Alendronate," *Bone*, 18(6): 621–627 (1996).

Frost, "Bone Histomorphometry: Analysis of Trabecular Bone Dynamics," *Bone Histomorphometry: Techniques and Interpretation*, Recker, ed., Boca Raton, FL, CRC Press, pp. 109–131 (1983).

Hyder et al., "Estrogen Action in Target Cells: Selective Requirements for Activation of Different Hormone Response Elements," *Mol. Cell. Endocrinol.*, 112: 35–43 (1995).

Jimenez et al., "Clomiphene Prevents Cancellous Bone Loss from Tibia of Ovariectomized Rats," *Endocrinology*, 138(5):1794–1800 (1997).

Jordan, "Biochemical Pharmacology of Antiestrogen Action," *Pharmacol. Rev.*, 36(4):245–276 (1984).

Jordan et al., "Geometric Isomers of Substituted Triphenylethylenes and Antiestrogen Action," *Endocrinology*, 108(4):1353–1361 (1981).

(List continued on next page.)

*Primary Examiner*—Gary Geist
*Assistant Examiner*—Leigh C. Maier
(74) *Attorney, Agent, or Firm*—Mueting, Raasch & Gebhardt, P.A.

(57) ABSTRACT

A method for treating symptoms, diseases and conditions in extra-reproductive tract tissues that are responsive to treatment with estrogen, using triarylethanes of formula (I)

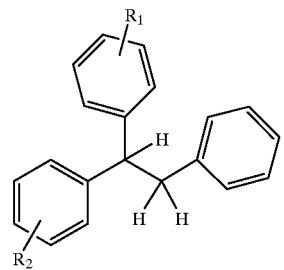

(I)

wherein $R_1$ is —O(CH$_2$)$_m$R$_3$ or —(CH$_2$)$_n$R$_3$; wherein $R_3$ is an anionic substituent; m is an integer from 1 to 4; and n is an integer from 0 to 4; and wherein $R_2$ is either H or —OH. Each of $R_1$ and $R_2$ can be either meta or para to its respective phenyl ethyl linkage. Compounds having the formula (I) wherein $R_1$ is —O(CH$_2$)$_m$R$_3$ or —(CH$_2$)$_n$R$_3$; $R_3$ is an anionic substituent; m is 1, 2, 3 or 4; n is 0, 1, 2, 3 or 4; $R_2$ is H or —OH; and wherein each of $R_1$ and $R_2$ is independently meta or para to its respective phenyl ethyl linkage are also provided, with the proviso that $R_2$ is not para —OH when m is 1 and $R_3$ is —COOH.

24 Claims, 6 Drawing Sheets

OTHER PUBLICATIONS

Ke et al., "Comparative Effects of Droloxifene, Tamoxifen, and Estrogen on Bone, Serum Chlosterol, and Uterine Histology in the Ovariectomized Rat Model" *Bone*, 20(1):31–39 (1997).

Ke et al., "Droloxifene, a New Estrogen Antagonist/Agonist, Prevents Bone Loss in Ovariectomized Rats," *Endocrinology*, 136(6):2435–2441 (1995).

Killackey et al., "Endometrial Adenocarcinoma in Breast Cancer Patients Receiving Antiestrogens," *Cancer Treat. Rep.*, 69(2):237–238 (1984).

Kohno et al., "Anti–estrogen Activity in the Yeast Transcription System: Estrogen Receptor Mediated Agonist Response," *Steroids*, 59:572–578 (1994).

Kraft et al. "3–Hydroxytriarylethylene Oxyacetic Acid: a Configurationally Defined Estrogen Antagonist in MCF–7 Cells," 214$^{th}$ ACS National Meeting, Las Vegas NV, Sep. 7–11, Abstract No. 202 (1997).

Kraft et al., "Carboxylic Acid Analogues of Tamoxifen: (Z)–2–[p–(1,2–diphenyl–1–butenyl)phenoxy]–N,N–dimethylethylamine. Estrogen Receptor Affinity and Estrogen Antagonist Effects in MCF–7 Cells," *J. Med. Chem.*, 42(16):3126–33 (1999) (entered into ACS CAPLUS electronic database on Jul. 26, 1999).

Kuiper et al., "Comparison of the Ligand Binding Specificity and Transcript Tissue Distribution of Estrogen Receptors α and β," *Endocrinology*, 138(3):863–870 (1997).

Love et al., "Bone Mineral Density in Women with Breast Cancer Treated with Adjuvant Tamoxifen for at least Two Years," *Breast Cancer Res. Treat.*, 12:297–302 (1988).

Lundeen et al., "Characterization of the Ovariectomized Rat Model for the Evaluation of Estrogen Effects on Plasma Cholesterol Levels," *Endocrinology*, 138(4):1552–1558 (1997).

Moon et al., "Dose–Dependent Effects of Tamoxifen on Long Bones in Growing Rats: Influence of Ovarian Status," *Endocrinology*, 129(3):1568–1574 (1991).

Onoe et al., "Expression of Estrogen Recpetor β in Rat Bone," *Endocrinology*, 138(10):4509–4512 (1997).

Ruenitz, "Female Sex Hormones and Analogs," *Burger's Medicinal Chemistry and Drug Discovery*, 5$^{th}$ Edition, Wolff, ed., vol. 4, New York, John Wiley & Sons, Ch. 57, pp. 553–587 (1997).

Ruenitz et al., "Specific Bone–Protective Effects of Metabolites/Derivatives of Tamoxifen and Clomiphene in Ovariectomized Rats," *Bone*, 23(6):537–542 (1998).

Ruenitz et al., "Acidic Metabolites of Tamoxifen—Aspects of Formation and Fate in the Female Rat," *Drug Metab. Dispos.*, 23(9):993–998 (1995).

Ruenitz et al., "Estrogenic Triarylethylene Acetic Acids: Effect of Structural Variation on Estrogen Receptor Affinity and Estrogenic Potency and Efficacy in MCF–7 Cells," *J. Med. Chem.*, 39:4853–4859 (1996).

Ruenitz et al., "Estrogenic Tamoxifen Derivatives: Categorization of Intrinsic Estrogenicity in MCF–7 Cells," *J. Steroid Biochem. Mol. Biol.*, 63(4–6):203–209 (1997).

Sato et al., "Raloxifene, Tamoxifen, Nafoxidine, or Estrogen Effects on Reproductive and Nonreproductive Tissues in Ovariectomized Rats," *FASEB J.*, 10:905–912 (1996).

Seoud et al., "Gynecologic Tumors in Tamoxifen–Treated Women With Breast Cancer," *Obstet. Gynecol.*, 82(2):165–169 (1993).

Shelby et al., "Assessing Environmental Chemicals for Estrogenicity Using a Combination of In Vitro and In Vivo Assays," *Environ. Health Perspect.*, 104(12):1296–1300 (1996).

(Abstract) Shen et al., "Bone Protective Effects of Nonsteroidal Estrogen Receptor (ER) Ligands in Ovariectomized Rats," *J. Bone Miner. Res.—1997 Program & Abstracts*,19$^{th}$ Annual Meeting of the American Society for Bone and Mineral Research, Cincinnati, OH, 12(1):p. S354, No. F514, Sep. 10–14 (1997).

Soto et al., "The E–Screen Assay as a Tool to Identify Estrogens: An Update on Estrogenic Environmental Pollutants," *Environ. Health Perspectives*, 103(Supp. 7):113–122 (1995).

Soto et al., "The Role of Estrogens on the Proliferation of Human Breast Tumor Cell (MCF–7)," *J. Steroid Biochem.*, 23(1):87–94 (1985).

Wang et al., "Molecular Effects of Genistein on Estrogen Receptor Mediated Pathways," *Carcinogenesis*, 17(2):271–275 (1996).

Williams et al., "Effects of Estrogen and Tamoxifen on Serum Osteocalcin Levels in Ovariectomized Rats," *Bone Mineral.*, 14:205–220 (1991).

Willson et al., "Dissection of the Molecular Mechanism of Action of GW5638, a Novel Estrogen Receptor Ligand, Provides Insights into the Role of Estrogen Receptor in Bone," *Endocrinology*, 138(9):3901–3911 (1997).

Wilson et al., "Estrogen Receptor Affinity and Effects on MCF–7 Cell Growth of Triarylethylene Carboxylic Acids Related to Tamoxifen," *J. Steroid. Biochem. Molec. Biol.*, 42(6):613–616 (1992).

Wronski et al., "Skeletal Effects of Withdrawal of Estrogen and Diphosphonate Treatment in Ovarectomized Rats," *Calcif. Tissue Int.*, 53:210–216 (1993).

Wronski et al., "Estrogen Treatment Prevents Osteopenia and Depresses Bone Turnover in Ovariectomized Rats," *Endocrinology*, 123(2):681–686 (1988).

Young et al., "A Short–Term Comparison of the Effects of Clomiphene Citrate and Conjugated Equine Estrogen in Menopausal/Castrate Women," *Int. J. Fertil.*, 36(3):167–171 (1991).

* cited by examiner

ESTROGEN MIMETICS LACKING REPRODUCTIVE TRACT EFFECTS

This application claims the benefit of U.S. Provisional Application No. 60/094,944, filed Jul. 31, 1998.

STATEMENT OF GOVERNMENT RIGHTS

This invention was made with the support of the U.S. Government under Grant No. AR 42069 from the National Institutes of Health. The Government may have certain rights in this invention.

BACKGROUND OF THE INVENTION

Estrogen deficiency is known to result in deterioration of the skeletal and cardiovascular systems in postmenopausal women. Osteoporosis is characterized by a progressive decrease in bone density which can lead to an increased incidence of bone fractures. This condition results when the rate of bone resorption exceeds that of bone formation. Several disorders induce abnormalities in bone remodeling, the most common of which is loss of gonadal steroid action, as can occur in menopause or in male or female hypogonadism. Thus, bone loss is not itself a disease but rather is a consequence of endocrine imbalance.

Several types of therapeutic agents are available or in development for use when estrogen replacement therapy (ERT) is indicated for prevention of postmenopausal bone loss. The most important of these suppress bone resorption and formation in a manner that maintains net bone balance, presumably as a consequence of interaction with estrogen receptors (ER) in osteoblasts and osteoclasts, cell types responsible for bone maintenance. Thus, 17β-estradiol and its orally active analogs, including conjugated equine estrogens, are widely used in ERT in postmenopausal women. The use of these steroids in ERT can, however, cause serious adverse effects on the reproductive system. For example, administration of 17β-estradiol is associated with increased risk of developing uterine cancer and endometriosis; there is also a possible link between estrogen use and breast cancer.

Steroidal estrogen substitutes such as ethynyl estradiol and mestranol have been used in ERT, but are also disfavored. These compounds have been associated with a number of adverse side effects including myocardial infarction, thromboembolism, cerebrovascular disease, and endometrial carcinoma. Fortunately, however, the estrogen receptor has been found to bind not only estradiol and other steroidal compounds but also a diverse array of aromatic nonsteroidal structural types, exemplified by mono- and dihydroxylated triarylethylenes. This observation has stimulated a significant amount of research in an effort to identify effective nonsteroidal compounds for use in ERT. Agents displaying bone-selective estrogenicity are of particular interest due to their potential for reduced reproductive tract toxicity compared with conventional estrogens. M. Sato et al., FASEB J. 10: 905–912 (1996); H. Ke et al., Endocrinology (Baltimore) 136: 2435–2441 (1995).

Some nonsteroidal estrogen antagonists have, somewhat surprisingly, showed promise in preventing bone loss in postmenopausal women. An example of such a nonsteroidal antiestrogen is tamoxifen (TAM), ((Z)-2-[4-(1,2-diphenyl-1-butenyl)phenoxy]-N,N-dimethylethanamine), which is a triphenylethylene derivative. Tamoxifen effectively antagonizes the growth-promoting effect of estrogens in primary target tissues such as the uterus and ovary. Tamoxifen is currently marketed for the treatment of breast cancer, and is also administered to initiate ovulation in anovulatory women. Adverse side effects, however, can include reproductive tract effects such as endometriosis and endometrial cancer (M. Killackey et al., Cancer Treat. Rep. 69: 237–238 (1985); M. Seoud et al., Obstet. Gynecol. 82: 165–169 (1993)). Clomiphene (CLO) (2-[4-(2-chloro-1,2-diphenylethenyl)phenoxy]-N,N-diethylethanamine), which is structurally close to tamoxifen, is another nonsteroidal antiestrogenic pharmaceutical compound that has been used in ERT. The preparation of clomiphene is described in U.S. Pat. No. 2,914,563. Clomiphene is prescribed to induce ovulation in infertile women with physiological indications of normal estrogen levels. In the hypothalamus, clomiphene antagonizes estradiol-mediated feedback inhibition of gonadotrophin-releasing hormone secretion.

Interestingly, although they antagonize the growth-promoting effect of estrogens in primary reproductive target tissues, the nonsteroidal antiestrogens CLO and TAM prevent development of osteopenia in the ovariectomized (OVX) rat to a degree approaching that of 17β-estradiol. Histomorphometric analysis of bone specimens from OVX rats receiving 17β-estradiol, or the nonsteroidal antiestrogens tamoxifen (TAM) or clomiphene (CLO) has shown a decreased rate of bone turnover and maintenance of normal bone mass for all three experimental groups compared to that observed in untreated OVX rats (M. Jimenez et al. Endocrinology 138:1794–1800 (1997); L. Moon et al., Endocrinology 129:1568–1574 (1991); T. Wronski et al., Endocrinology 123:681–686 (1988). Likewise, estrogen or TAM administration to OVX rats resulted in decreased serum levels of osteocalcin (D. Williams et al., Bone Mineral. 14:205–220 (1991)). Osteocalcin is a bone matrix protein which is released into the serum during bone formation, thus serving as a specific indicator of bone turnover. TAM and CLO have also been shown to prevent bone loss in postmenopausal women (R. Love et al., Breast Cancer Res. Treat. 12:297–302 (1988); R. Young et al., Int. J. Fertil. 36:167–171 (1991)). In contrast to 17β-estradiol, however, CLO and TAM are only moderately uterotrophic. U.S. Pat. No. 4,894,373 to Young describes the use of clomiphene, tamoxifen, nafoxidene, and other antiestrogenic compounds in the treatment of menopause and osteoporosis. However, despite results suggesting that these compounds are less estrogenic in reproductive tissues than steroidal estrogens, the adverse reproductive tract effects of tamoxifen, raloxifene, and other nonsteroidal antiestrogens (V. Jordan, Pharmacol. Rev. 36:245–276 (1984), T. Willson et al., Endocrinology 138:3901–3911 (1997)) are problematic.

Nonsteroidal estrogenic compounds are also of interest in the continuing effort to improve ERT. However, the use of nonsteroidal estrogenic compounds, like estradiol, in ERT is expected to be accompanied by a detrimental effect on the reproductive tract. For example, compounds that are estrogenic (growth-promoting) in MCF-7 cells, such as diethylstilbestrol (DES) and chlorotrianisene, are known to cause undesirable uterotrophic effects in the OVX rat (P. Ruenitz et al., J. Steroid Biochem. Mol. Biol., 63, 203–209 (1997); M. Shelby et al., Environ. Health Perspect., 104, 1296–1300 (1996)).

An estrogen mimetic that showed initial promise for use in ERT, based upon findings that suggested it could be selectively estrogenic in nonreproductive tissues (P. Ruenitz et al., J. Med. Chem. 39:4853–4859 (1996)) was 4-hydroxytamoxifen acid, a nonsteroidal metabolite of tamoxifen (4HTA; (E,Z)-2-{4-[1-(p-hydroxyphenyl)-2-phenyl]-1-butenyl}phenoxyacetic acid). 4HTA was shown in U.S. Pat. No. 5,189,212 to have estrogenic activity, a result that was quite unexpected since both the parent compound tamoxifen and the related compound clomiphene have an opposite, antiestrogenic effect in vivo. ER affinity, estrogenic (i.e., growth stimulatory) potency and estrogen efficacy were compared for a group of synthetic monophenolic triarylethylene acetic acids and analogs that included 4HTA (P. Ruenitz et al., J. Med. Chem. 39:4853–4859 (1996)). These synthetic compounds were designed to evaluate the importance of structural features known or anticipated to facilitate ER affinity. 4HTA was shown to have high ER affinity and strong growth stimulatory potency (estrogenicity) in MCF-7 breast cancer cells. In addition, 4HTA functioned as a partial agonist in stimulating growth (79% maximal growth-stimulatory effect, as a percent of that of estradiol) in the MCF-7 cell proliferation assay, while exhibiting weak antagonist potency in an inhibition assay in the presence of estrogen (P. Ruenitz et al., J. Med. Chem. 39:4853–4859 (1996); S. Wilson et al., J. Steroid Biochem. Molec. Biol. 42:61314 616 (1992)). It was also reported that 4HTA exhibited an effect on trabecular bone maintenance that was qualitatively similar to that of estradiol, yet that it had no observable uterotrophic effect. Taken together, these characteristics suggested the possibility of differential estrogenicity for 4HTA; however we subsequently discovered, as disclosed herein, that 4HTA is moderately uterotrophic and that it does not have a bone protective effect.

A saturated analog of 4HTA, 4-[1-(4-hydroxyphenyl)-2-phenylethyl]phenoxyacetic acid (HPPA), was also evaluated by P. Ruenitz et al. (J. Med. Chem. 39:4853–4859 (1996)). In contrast to its parent compound, HPPA exhibited unpromising ER affinity. However, despite its relatively low ER affinity, HPPA exhibited estrogenic potency approaching that of 4HTA in MCF-7 cells. HPPA also was a full agonist in stimulating growth (102% maximal growth-stimulatory effect, as a percent of that of estradiol) and did not function as an estrogen antagonist in the growth inhibition assay. Growth-promoting effects of both 4HTA and HPPA were fully antagonized by the antiestrogen tamoxifen, suggesting that such effects are mediated via ER (P. Ruenitz et al., J. Med. Chem. 39:4853–4859 (1996)). That report did not investigate the level of extra-reproductive tract estrogenicity, if any, of the compounds under study.

What is needed for use in ERT is an estrogen mimetic having selective estrogenicity which, like estrogen, counteracts the skeletal and cardiovascular deterioration that often accompanies menopause, but lacks the reproductive tract effects typically associated with currently available estrogens and antiestrogens.

SUMMARY OF THE INVENTION

The invention provides a method for treating symptoms, diseases and conditions in extra-reproductive tract tissues that are responsive to treatment with estrogen, using triarylethanes of formula (I)

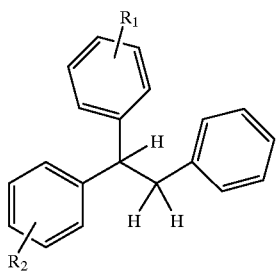

(I)

wherein $R_1$ is —O(CH$_2$)$_m$R$_3$ or —(CH$_2$)$_n$R$_3$; wherein $R_3$ is an anionic substituent; m is 1, 2, 3 or 4; and n is 0, 1, 2, 3 or 4; and wherein $R_2$ is either H or —OH. Each of $R_1$ and $R_2$ can be either meta or para to its respective phenyl ethyl linkage.

An anionic substituent is a substituent that has at least one functional group having a partial or complete negative charge under physiological conditions. Physiological conditions are those found in the mammalian body and are typified by 0.1 M sodium phosphate buffer, pH 7.4. Where the functional group having a partial or complete negative charge under physiological conditions is an acidic group, it is to be understood that the acidic group can be present in its protonated (free acid) or unprotonated form (e.g., —COOH and —COO⁻), or can carry a partial charge.

The anionic substituent preferably includes a carboxylate group, a tetrazolate group or a bisphosphonate group. One preferred embodiment of the method utilizes the compound of formula I wherein the anionic substituent comprises carboxylate group (—COO⁻; pK$_a$ about 3.1). Another preferred method utilizes the compound of formula I wherein the anionic substituent comprises a tetrazolate group (—CN$_4$H) which has a pK$_a$ of about 6 (D. Carini et al., J. Med. Chem. 34:2525–47 (1991)); e.g., compound 3 as shown in FIG. 1, which is formula I wherein $R_1$=—OCH$_2$R$_3$, $R_3$=—CN$_4$H and $R_2$ is para to its phenyl ethyl linkage. Yet another preferred method utilizes the compound of formula I wherein the anionic substituent comprises a bisphosphonate (—C(PO$_3^{-2}$)$_2$ OH); e.g., compound 4 as shown in FIG. 1, which is formula I wherein $R_1$=—OCH$_2$R$_3$, $R_3$=—C(PO$_3^{-2}$)$_2$ OH and $R_2$ is para to its phenyl ethyl linkage. Where the anionic substituent comprises a bisphosphonate group, the bisphosphonate group is preferably nonhydrolyzable; i.e., the bisphosphonate moiety cannot be cleaved off of the triarylethyl nucleus under physiologic conditions.

A preferred method of the invention utilizes the compound of formula I wherein $R_2$ is p-hydroxyl, for example 4-[1-(4-hydroxyphenyl)-2-phenylethyl]phenoxyacetic acid (HPPA; 1, FIG. 1; formula I wherein $R_1$ is —OCH$_2$R$_3$; $R_3$ is —COO⁻; and $R_2$ is —OH, wherein both $R_1$ and $R_2$ are para to their respective phenyl ethyl linkages).

In another preferred embodiment, the method of the invention utilizes the compound of formula I wherein $R_2$ is H, for example 4-(1-phenyl-2-phenylethyl)phenoxyacetic acid (PPA; 2, FIG. 1; formula I wherein $R_1$ is —OCH$_2$R$_3$; $R_3$ is —COO⁻; and $R_2$ is H; such that both $R_1$ and $R_2$ are para to their respective phenyl ethyl linkages).

The compound of formula I includes each of the enantiomeric forms resulting from the chirality of the diarylmethine carbon, and is further intended to include a racemic mixture of these enantiomers. "Extra-reproductive tract tissues" that are responsive to treatment with estrogen include bone, cardiovascular tissue, liver tissue, and central nervous system tissue.

The method of the invention is particularly useful for treating skeletal and/or cardiovascular symptoms associated with ovarian estrogen deficiency. Estrogen deficiency in a mammal can result, for example, from menopause or hypogonadism. Skeletal symptoms or conditions that are associated with estrogen deficiency and are thus treatable in accordance with the method of the invention include those resulting from osteopenia, such as osteoporosis. High serum cholesterol is an example of a cardiovascular condition associated with estrogen deficiency that can be treated in accordance with the method of the invention. It will be appreciated that the method of the invention is generally useful to treat any condition or symptom in a nonreproductive tissue that is associated with or caused by a deficiency of estrogen, particularly if that condition or symptom would be expected to respond to the administration of estrogen. Thus, other conditions that can be alleviated by administration of the compound of formula I include vasomotor symptoms associated with menopause and various symptoms associated with estrogen deficiency caused by female hypogonadism and primary ovarian failure.

The use of the nonsteroidal compounds of formula I to treat conditions, symptoms and diseases associated with estrogen deficiency avoids the undesirable side effects that accompany current estrogen replacement therapies. Moreover, administration of the compound of formula I is preferably accompanied by little or no effect on the reproductive tract of the mammal, making the compound particularly well-suited for use in estrogen replacement therapy in perimenopausal or postmenopausal women.

Preferably, the method of the invention comprises administering to a patient an amount of the compound of formula I effective to prevent or reduce cancellous bone loss in the patient. More preferably, the active compound is administered in an amount effective to also reduce the patient's serum cholesterol levels. The patient is preferably a female patient, more preferably a perimenopausal or postmenopausal female human patient.

The nonsteroidal estrogenic triarylethanes of formula I are administered to a patient as the free acid or as a pharmaceutically acceptable salt in combination with pharmaceutical carriers suitable for topical, subcutaneous, intramuscular, intravenous, oral administration, or the like.

The invention further provides a composition comprising a compound of formula I and a pharmaceutically acceptable carrier.

Also provided by the invention is a compound of formula I wherein $R_1$ is —O(CH$_2$)$_m$R$_3$ or —(CH$_2$)$_n$R$_3$; $R_3$ is an anionic substituent as defined above; m is 1, 2, 3 or 4; n is 0, 1, 2, 3 or 4; $R_2$ is H or —OH; and wherein each of $R_1$ and $R_2$ is independently meta or para to its respective phenyl ethyl linkage; provided that $R_2$ is not para —OH when m is 1 and $R_3$ is —COOH (P. Ruenitz et al., J. Med. Chem. 39:4853–4859 (1996)).

DETAILED DESCRIPTION OF THE INVENTION

Abbreviations

Figure 1:
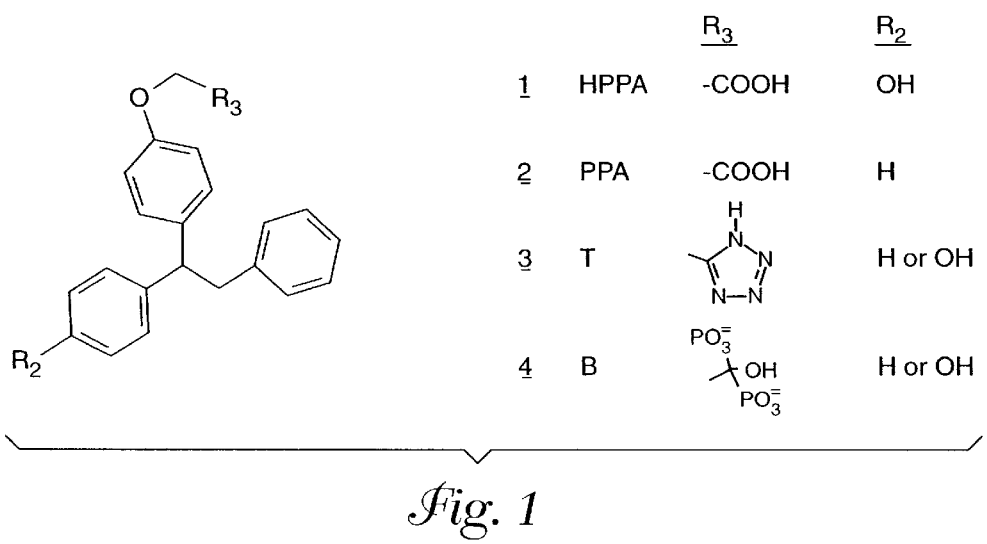
FIG. 1. Structures of HPPA 1, PPA 2, and their tetrazole (T) 3 and bisphosphonate (B)4 derivatives.

The following abbreviations are used throughout the specification: ER, estrogen receptor; ERT, estrogen replacement therapy; OVX, ovariectomized; TAM, tamoxifen ((Z)-2-[4-(1,2-diphenyl-1-butenyl)phenoxy]-N,N-dimethylethanamine); CLO, clomiphene (2-[4-(2-chloro-1,2-diphenylethenyl)phenoxy]-N,N-diethylethanamine); 4-hydroxy CLO, 4-hydroxyclomiphene (4-[1-(p-hydroxyphenyl)-2-phenyl-2-chloroethenyl]phenoxyethyl-N,N-diethylamine); 4HTA, 4-hydroxytamoxifen acid ((E,Z)-2-{4-[1-(p-hydroxyphenyl)-2-phenyl]-1-butenyl}phenoxyacetic acid); HPPA, 4-[1-(4-hydroxyphenyl)-2-phenylethyl]phenoxyacetic acid (also sometimes referred to as D4HTA); and PPA, 4-(1-phenyl-2-phenylethyl)phenoxyacetic acid; $EC_{50}$ and $ED_{50}$, the effective concentration or dose, respectively, of a test compound in an assay to reach 50% maximal effect compared to a reference compound (herein, typically β-estradiol); essentially a measurement of the potency of the test compound, with lower values signifying greater potency.

Estrogenicity

Cultured human and animal cells naturally endowed with ER have been widely used in characterizing effects of steroidal and nonsteroidal ER ligands. In particular, the MCF-7 cell line, derived from a human breast cancer, has become established in regard to assessment of estrogenic potency and efficacy (see, e.g., P. Ruenitz et al., J. Steroid. Biochem.

Molec. Biol. 63:203–209 (1997), citing E. Bignon et al., J. Med. Chem. 32: 2092–2103 (1989) and A. Soto et al., Environ. Health Perspectives 103: 112–122 (1995)). In MCF-7 cells, biotransformation of ER ligands is rarely significant, which simplifies interpretation of results. Estrogenicity in such cells is due to interaction of liganded ER with composite estrogen response elements (ERE) in DNA, rather than with only classical palindromic ERE as appears to be the case in ER-transfected cell lines (P. Ruenitz et al., J. Steroid. Biochem. Molec. Biol. 63:203–209 (1997), citing H. K-OHno et al., Steroids 59: 572–578 (1994) and S. Hyder et al., Mol. Cell. Endocrinol. 112: 35–45 (1995)). The MCF-7 cell environment thus more closely approximates the complex cellular environment found in mammalian organisms, compared to nonmammalian ER-transfected cells.

The effects of compounds on MCF-7 cell growth are not always consistent with effects seen in animals or humans. Thus, genistein, a flavone with ER affinity and MCF-7 cell growth, stimulatory potency/efficacy similar to that of 4HTA and its analogs, is considered to be a cancer preventative agent (T. Wang et al., Carcinogenesis 17:271–275 (1996)). In contrast, N-[(p-benzylphenoxy)diethylamine was an inhibitor of MCF-7 growth, but was a cancer-promoting agent in the rat L. Brandes et al., Cancer Res. 48: 3954–3958 (1988)). It is therefore important to evaluate potentially therapeutic estrogen mimetics using in vivo models of extra-reproductive tract estrogenicity.

Animal Model

The OVX rat is an established animal model for investigating mechanistic aspects of skeletal (T. Wronski et al., Endocrinology 123:681–686 (1988)), cardiovascular (S. Lundeen et al., Endocrinology 138:1552–1558 (1997)), and reproductive organ (M. Jimenez et al., Endocrinology 138:1794–1800 (1997)) effects of ER ligands. The effects of many steroidal and nonsteroidal ER ligands have been studied in this system, such as TAM, estradiol, raloxifene and droloxifene.

Estrogen Receptor (ER) Affinity

It should be noted that ER consists of two isoforms, designated ERα and ERβ. It is unlikely that HPPA (or its analogs) has differential affinity for the ER isoforms, based on reported similarity of human ERα and rat ERβ affinities of close structural analogs (G. Kuiper et al., Endocrinology 138:863–870 (1997)). Moreover, ERα and ERβ were detected in a ratio of about 3:1 in rat uterine tissue (G. Kuiper et al., Endocrinology 138:863–870 (1997)), and both isoforms were found in osteoblasts (Y. Onoe et al., Endocrinology 138:4509–4512 (1997)). Collectively, these findings suggest that HPPA's differential skeletal vs. uterine effects are not a consequence of its ability to interact with only one of the ER isoforms. Functionally active human ERα is commercially available from Panvera Inc., Madison Wis. and is routinely used for comparative ER affinity studies, recognizing that absolute values obtained might differ somewhat from those that would be observed for ERα and ERβ together.

Characterization and Comparison of HPPA and 4HTA

HPPA and its unsaturated analog 4HTA differ in their relative estrogen receptor binding affinities (RBA), exhibiting RBAs of 0.20 and 20 percent of estradiol binding affinity, respectively (P. Ruenitz et al., J. Med. Chem. 39: 4853–4859 (1996)). Nonetheless, both HPPA and 4HTA are potent stimulators of cell proliferation in MCF 7 human breast cancer cells, and HPPA, although it exhibits a relatively low estrogen receptor affinity, is considered a "full estrogen" by virtue of its ability to eventually stimulate maximal growth of MCF 7 cells to a level equal to that attained by estradiol (P. Ruenitz et al., J. Med. Chem. 39: 4853–4859 (1996)). Additionally, 4HTA is a mild antiestrogen in that it weakly inhibits estradiol-stimulated proliferation of MCF 7 human breast cancer cells; in contrast, HPPA shows no activity as an antiestrogen.

The two compounds also differ in their effect on bone tissue in vivo. Despite its high estrogen receptor affinity and estrogenic potency in stimulating MCF-7 cell proliferation, 4HTA shows no bone protective effect in the OVX rat, contrary to the erroneous report in P. Ruenitz et al. (J. Med. Chem. 39: 4853–4859 (1996)); it is ineffective in preventing loss of cancellous bone volume or elevation of serum osteocalcin after ovariectomy (see Example III). HPPA, on the other hand, shows significant bone protective estrogenicity. Moreover, and very advantageously, HPPA has been discovered to be nonuterotrophic. This stands in contrast to 4HTA, which is, in fact, moderately uterotrophic, notwithstanding statements to the contrary in P. Ruenitz et al., J. Med. Chem. 39: 4853–4859 (1996). The finding that HPPA is not uterotrophic was quite unexpected in view of the reproductive tract effects that routinely accompany the administration of other known estrogens and estrogenic compounds (Table 1).

TABLE 1

Estrogens that stimulate MCF-7 cell growth are uterotrophic in the rat, except HPPA.

| Estrogen | MCF-7 Cell Growth | | Rat Uterotrophic Assay | | REF. |
| --- | --- | --- | --- | --- | --- |
| | $EC_{50}$, nM[a] | % Efficacy | $ED_{50}$, μg/day[b] | % Efficacy | |
| 17β-estradiol | 0.02 | 100 | 0.16 | 100 | 3, 5 |
| diethylstilbestrol (DES) | 0.03 | 100 | 3[c] | 100 | 4, 7 |
| trans-tamoxifen[d] | 0.11 | 21 | 10 | 12 | 3, 5 |
| cis-tamoxifen | 11 | 100 | 40 | 52 | 3, 5 |
| HPPA | 16 | 100 | >3400 | 0 | 1, 2, Ex. III |
| chlorotrianisene | 28 | 89 | 40[c] | 100 | 1, 6 |

[a]The concentration at which growth stimulation was 50% maximal.
[b]The dose at which uterine weight gain was 50% maximal.
[c]Determined in the mouse.
[d]This substance is a partial estrogen mimetic.

REFERENCES
(Table 1)
1. P. Ruenitz et al., J. Steroid Biochem. Mol. Biol. 63: 203–209 (1997).
2. Y. Shen et al., J. Bone Miner. Res. 12: S354, 19th Annual American Society of Bone and Mineral Research Meeting, Cincinnati Ohio, Sep. 10–14, 1997, No. F514.
3. E. Bignon et al., J. Med. Chem. 32: 2092–2103 (1989).
4. A. Soto et al., J. Steroid Biochem. 23: 87–94 (1985).
5. V. Jordan et al., Endocrinology 108: 1353–1361 (1981).
6. C. Emmens et al., J. Endocrinol. 5: 170–173 (1947).
7. M. Shelby et al., Environ. Health Perspect. 104: 1296–1300 (1996).

Pharmaceutical Compositions

Administration of the nonsteroidal estrogenic triarylethyl compound of formula I can take any convenient form. For example, the active compound can be administered orally, topically, parenterally (including subcutaneous, intramuscular and intravenous administration), vaginally, rectally, nasally, ophthalmically, intraperitoneally or via implantable extended release devices. Oral administration is preferred. The active compound of formula I can be administered as the free acid or as a pharmaceutically acceptable salt, including the sodium, potassium, or tromethamine salt. The active compound can be combined with acceptable pharmaceutical carriers or diluents. Pharmaceutically acceptable carriers and methods for the combining active compounds with such carriers are known and will be obvious to one skilled in the art.

The therapeutic composition can be formulated in any convenient manner as prescribed by the selected mode of administration, for example as a tablet, capsule, suppository, or injection. Formulations of the present invention suitable for oral administration may be presented as discrete units such as tablets, troches, capsules, pills, lozenges, wafers, or cachets, each containing a predetermined amount of the compound of formula I as a powder or granule, or as a suspension in an aqueous liquor or nonaqueous liquid such as a syrup, an elixir, an emulsion or a draught. The compounds of formula I can be incorporated into liposomes.

Liposomes may be prepared according to methods known to those skilled in the art, for example, as described in U.S. Pat. No. 4,522,811.

The active compound may be incorporated into controlled or sustained release preparations or devices. Biodegradable, biocompatible polymers, such as polyanhydrides, ethylene vinyl acetate, polyglycolic acid, can be used to control the rate of release of the active ingredient in the body.

The tablets, troches, pills, capsules, and the like may also contain one or more of the following: a binder such as microcrystalline cellulose, gum tragacanth, acacia, corn starch or gelatin; an excipient such as dicalcium phosphate, starch or lactose; a disintegrating agent such as corn starch, potato starch, alginic acid and the like; a lubricant such as magnesium stearate; a glidant such as colloidal silicon dioxide; a sweetening agent such as sucrose, fructose, lactose, saccharin or aspartame; a natural or artificial flavoring agent such as peppermint, methyl salicylate, or orange flavoring; and/or an adjuvant material. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. When the dosage unit form is a capsule, syrup, elixir, or suspension it can contain, in addition to material of the above type, a liquid carrier such as a fatty oil; a preservative such as methyl- or propylparaben; an agent to retard crystallization of the sugar; an agent to increase the solubility of any other ingredient, such as a polyhydric alcohol, for example glycerol or sorbitol; and/or a dye. The material used in preparing any unit dosage form is substantially nontoxic in the amounts employed.

A preparation suitable for parenteral administration may contain a diluent such as water, ethanol, a polyol (such as glycerol, glycerine, propylene glycol, liquid polyethylene glycols, and the like), vegetable oil, glycerol ester, and mixtures thereof. Such a preparation can contain dispersions of sterile powders comprising the compound of formula I, which are preferably isotonic with the blood of the recipient. Isotonic agents that can be included in the liquid preparation include sugars, buffers (such as phosphate, acetate and citrate), and sodium chloride. If administered intravenously, preferred carriers are physiological saline or phosphate buffered saline (PBS). Solutions of the compound of formula I can be prepared in water, optionally mixed with a nontoxic surfactant. The ultimate dosage form is sterile, fluid and stable under the conditions of manufacture and storage. The necessary fluidity can be achieved, for example, by using liposomes, by employing the appropriate particle size in the case of dispersions, or by using surfactants. Sterilization of a liquid preparation can be achieved by any convenient method that preserves the bioactivity of the compound of formula I, preferably by filter sterilization. Preferred methods for preparing powders include vacuum drying and freeze drying of the sterile injectable solutions. Subsequent microbial contamination can be prevented using various antimicrobial agents, for example, antibacterial, antiviral and antifungal agents including parabens, chlorobutanol, phenol, sorbic acid, thimerosal, and the like. Absorption of the compound of formula I over a prolonged period can be achieved by including agents for delaying, for example, aluminum monostearate and gelatin.

Nasal spray formulations comprise purified aqueous solutions of the compound if formula I with preservative agents and isotonic agents. Such formulations are preferably adjusted to a pH and isotonic state compatible with the nasal mucous membranes.

Formulations for rectal or vaginal administration may be presented as a suppository with a suitable carrier such as cocoa butter, or hydrogenated fats or hydrogenated fatty carboxylic acids.

The therapeutic composition can also be administered topically for absorption through the skin. Formulations suitable for topical use include liquids, lotions, salves, gels, ointments, cremes, and the like. The active compounds can be combined with pharmaceutical creams or ointments. Methods for introducing the formulations via each of these routes are well-known in the art. Topical formulations typically comprise the compound of formula I dissolved or suspended in one or more media such as mineral oil, petroleum, polyhydroxy alcohols or other bases used for topical pharmaceutical formulations. Preparations intended for topical administration preferably contain about 0.01 wt-% to about 10 wt-% of the active compound in a liquid suspension, more preferably about 0.1 wt-% to about 1 wt-% active compound in the liquid suspension (the term "wt-%" as used herein means grams of active compound per 100 mL liquid). Other types of topical formulations (cremes, gels, and the like) can contain from about 0.01% to about 25%, by weight, of the active compound; preferably they contain about 1% to about 10%, by weight, of the active compound.

In addition to the aforementioned ingredients, the active compounds can be further mixed with other active materials that do not impair the estrogenic activity of the active compounds in nonreproductive tissues, including antibiotics, antifungals, antivirals, anti-inflammatories, and preservatives (such as antioxidants).

The compound of formula I is administered in an amount effective to prevent or reduce cancellous bone loss in a patient. Alternatively or additionally, the amount administered is effective to maintain normal serum cholesterol levels in a patient. One of skill in the art will appreciate that the dose of the active compound will vary depending upon the particular route of administration used. Typically, the compounds are administered in the range of 10 mg/day to 1000 mg/day, and more preferably between 20 and 40 mg/day, or 0.15 to 15 mg/kg of body weight per day, and preferably between 0.3 and 1.0 mg/kg of body weight per day. It will be appreciated that the effective dosage and mode of administration vary depending on the patient to be treated, the nature of the condition to be treated, and the severity of the condition to be treated. The effective dosage and mode of administration suitable for a particular patient having a particular medical need is readily ascertainable by one skilled in the art. For example, useful dosages of the active compound can be determined by comparing their in vitro activity and the in vivo activity in animals models. Methods for extrapolation of effective dosages in mice, and other animals, to humans are known in the art; for example, see U.S. Pat. No. 4,938,949.

EXAMPLES

The present invention is illustrated by the following examples. It is to be understood that the particular examples, materials, amounts, and procedures are to be interpreted broadly in accordance with the scope and spirit of the invention as set forth herein.

Example I
Synthesis of 4-[1-(p-hydroxyphenyl)-2-phenylethyl] phenoxyacetic Acid (HPPA) and 4-(1-phenyl-2-phenylethyl) phenoxyacetic Acid (PPA)

HPPA {4-[1-(p-hydroxyphenyl)-2-phenylethyl] phenoxyacetic acid} was prepared as previously described using the procedure set forth in P. Ruenitz et al., J. Med. Chem., 39, 4853–4859 (1996), incorporated herein by reference in its entirety (see Scheme 1).

Scheme 1

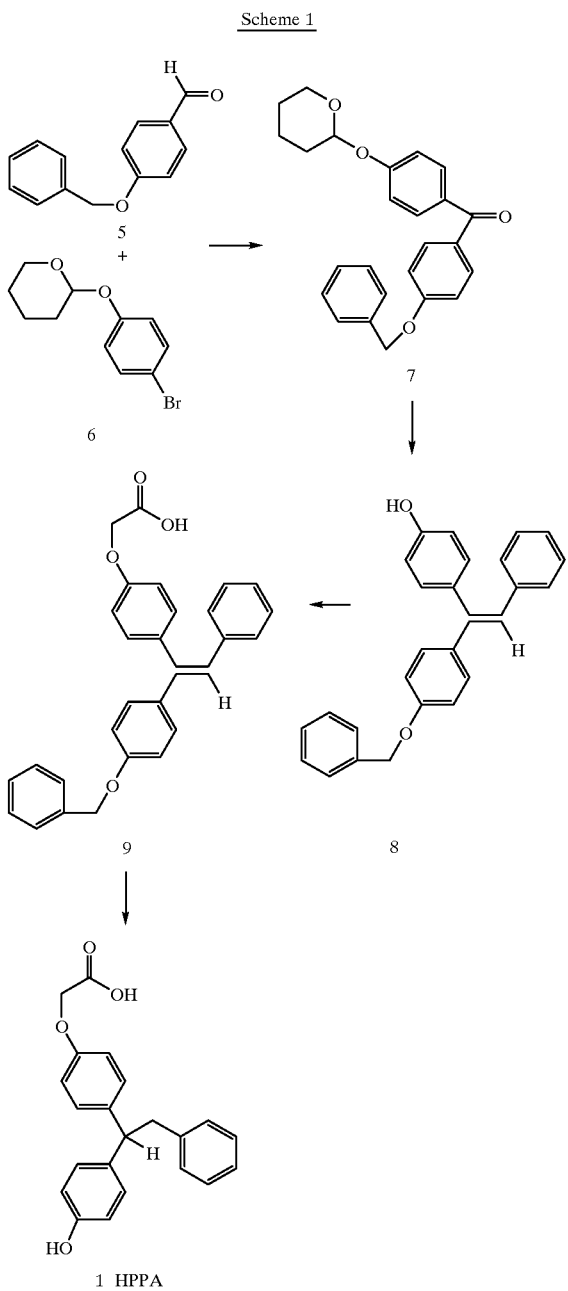

Experimental Procedures

Infrared (IR) and 400 MHz $^1$H NMR spectra were recorded in turn on Nicollet 510P FT-IR and Bruker AMX 400 spectrometers. NMR chemical shifts (δ) were determined using tetramethylsilane as standard. Mass spectra were obtained using a Perkin Elmer Sciex API 1plus mass spectrometer. Melting points were determined using an Electrothermal 9100 apparatus. Reaction progress, column chromatographic fractions, and purity of products were analyzed qualitatively by analytical TLC using 0.25 mm Analtech silica gel GF254 plates. Plates were developed with Solvent 1 [benzene-chloroform (50-50, v/v)], Solvent 2 [chloroform-methanol-28% aqueous ammonia (90-10-0.5, v/v)], or Solvent 3 [chloroform-isopropanol-glacial acetic acid (90-10-0.5, v/v)]. Developed plates were viewed under light of 254 nm wavelength. Reactions involving air-sensitive reagents were run under dry nitrogen gas. Chromatographic mobilities of compounds are expressed as $R_f$ values. Reaction mixture solutions in ether were generally worked up by removal of excess water with anhydrous sodium sulfate, followed by filtration and concentration in vacuo. In some cases redissolution of product residues in benzene followed by reconcentration in vacuo was carried out to remove residual water.

Starting Materials

Benzyl ether 5 was obtained from Aldrich Chemical Co. Tetrahydropyran-2-yl (THP) ether 6 was prepared by stirring a mixture of 1.73 g (10 mmols) of p-bromophenol with 10 mL of dihydropyran to which was added a small crystal of p-toluenesulfonic acid. After 1 hour, 50 mL of ether was added, and the solution was washed with two 20 mL portions of 5% aqueous NaOH, and then 20 mL of water. After adding 25 μL of triethylamine, workup gave 2.5 g (97%) of a colorless syrup which crystallized on storage at 8° C.

p-(Tetrahydropyran-2-yl)oxy-p'-benzyloxybenzophenone (7)

A small (0.5–1 mL) portion of a solution of 5 g (19.6 mmol) of 6 in 17 mL of tetrahydrofuran was added to 0.54 g (22.5 mg-atoms) of magnesium turnings, to which a few drops of dibromoethane and an iodine crystal had been added. After ca. 1 hour of intermittent stirring, a mild exothermic reaction started. The remainder of the solution of 6 was added dropwise to the stirred mixture at a rate so as to maintain reaction momentum. Then the mixture was heated at reflux for 1 h. The clear grey solution was cooled to 0° C., and a solution of 3.74 g (17.6 mmols) of 5 in 15 mL of tetrahydrofuran was added dropwise. The mixture was refluxed for 2 hours. The reaction solution was cooled in ice, and 4.0 mL of 30% NH$_4$Cl (9.2 mmols) was added slowly. The supernatant was decanted from precipitated salts and was concentrated in vacuo to give a yellow syrup which solidified on storage at 8° C. This was mixed with petroleum ether, filtered, and washed with this solvent to give 6.91 g (100%) of a light orange powder: TLC (Solvent 1) one spot, $R_f$ 0.14. This intermediate (17.8 mmols) was dissolved in 70 mL of methylene chloride and 5.13 g (13.6 mmols) of pyridinium dichromate was added. The mixture was stirred for 32.5 hours. The mixture was concentrated in vacuo, and the residue was extracted with four 30-mL portions of ether. The combined extracts were filtered and concentrated in vacuo to give 6.81 g (99%) of 7 as a gold oil: IR (neat, NaCl) 1650 cm$^{-1}$ (C=O).

Preparation of 8

7 (4.62 g, 12 mmols) was reacted with a 1.5 molar excess of benzylmagnesium chloride. The resulting carbinol was dissolved in 15 mL of ethanol and 2.5 mL of 5% HCl was added. After 1.5 hour, 20 mL of ether and 3 mL of 10% aqueous sodium carbonate was added, and the mixture was worked up, affording 5.45 g of a brown oil. This was chromatographed on 38 g of 60–200 mesh silica gel, with benzene as eluent. The first 125 mL of eluate was discarded. The next 170 mL was collected and concentrated in vacuo to give 5.04 g (112%) of 8 as a light yellow oil which solidified on storage at 8° C. A 200 mg sample of this was further purified by washing with two 5-mL portions of hexanes, followed by trituration with 5 mL of methanol. The precipitate was collected and washed with cold methanol to give 57 mg of 8 as a white powder: TLC (serial development two times with Solvent 1) one spot, $R_f$ 0.39; mp 129–132° C. Anal. (C$_{27}$H$_{22}$O$_2$) C, H.

Conversion of the Triarylethylene Monophenol 8 to the Oxyacetic Acid 9

The triarylethylene monophenol 8 was converted to 9 using a standard procedure as exemplified in P. Ruenitz et al., J. Med. Chem. 39: 4853–4859 (1996), for the synthesis of a dibenzyl ether. Briefly, to a solution of about 1 g of 8 in 25 mL of acetone was added about 1.86 g (1.25 mL, 11.13 mmols) of ethyl bromoacetate and about 0.78 g (5.56 mmols) of potassium carbonate. The mixture was stirred and refluxed for 6 hours, after which time TLC (Solvent 1) indicated a major component and the absence of 8. The cooled mixture was filtered and concentrated. The resulting yellow syrup was dissolved in 19 mL dioxane and 10 mL of 5% NaOH was added. After 0.5 hours, the solution was cooled in ice and 7 mL of 10% HCl was added. The resulting suspension was extracted with three 40-mL portions of ether. Workup left a white solid. In order to remove residual bromoacetic acid, this was mixed with 10 mL of acetone and then 20 mL of water was added. The mixture was filtered and washed with cold acetone-water (10–20, v/v). Drying (60° C., 0.05 mm Hg, 4 hours) gave about 1 g of halogen-free white powder: TLC (Solvent 3) one spot.

The benzyl ether 9 was obtained as white crystals from chloroform (25%): mp 143–147° C.; TLC (Solvent 3) two components of equal intensity, $R_f$ 0.38 and 0.44; $^1$H NMR (acetone-$d_6$) δ 4.57 and 4.73 (s, ca. 1 each, $OCH_2C\!=\!O$), 4.93 and 5.13 (s, ca. 1 each, $OCH_2Ar$), 6.55–7.38 (m, 18, ArH).

Hydrogenolysis/hydrogenation of 9

A solution of 1.46 g (3.34 mmols) of 9 in 100 mL of methanol was shaken with 0.16 g of 10% palladium on carbon for 2 hours under 44 psi of $H_2$. The mixture was filtered. The filtrate was concentrated in vacuo and the residue was dissolved in 10 mL of dioxane. The solution was diluted with 4 mL of 5% NaOH. After 0.5 h, the mixture was cooled in ice, acidified with 4 mL of 10% HCl, and extracted with 50 mL of ether. The extract was washed with 30 mL of water. Addition of 10 mL of benzene, followed by workup, gave 1.83 g of a gold oil. This was dissolved in 1 mL of dry chloroform, and the solution was diluted with 25 mL of hexanes. The resulting precipitate solidified on storage at 8° C. This was crystallized from 3 mL of alcohol-free chloroform to give a total of 0.78 g (67%) of 1 (HPPA) as beige crystals after drying at room temperature for 16 hours (0.05 mm Hg): mp 143–148° C. (subl); TLC (Solvent 3) one spot, $R_f$ 0.23; $^1$H NMR (acetone-$d_6$) δ 3.30 (d, J=8 Hz, 2, $CH_2Ph$), 4.21 (t, J=8 Hz, 1, $CHAr_2$), 4.62 (s, 2, $OCH_2$), 6.75 ("t", J=9 Hz, 4, $C_6H_4$—OH), 7.05–7.25 (m, 9, remaining ArH), 8.30 (s, 1, ArOH). Anal. ($C_{22}H_{20}O_4$·0.5 $H_2O$) C, H.

PPA 2, the deshydroxy counterpart of HPPA, is synthesized using an analogous synthetic scheme, except that in place of the benzyl ether 5, benzaldehyde is used as the starting material.

Example II

Synthesis of Tetrazole and Bisphosphonate Derivatives of HPPA and PPA

The tetrazole (T) derivative of PPA (FIG. 1; 3, where $R_2$=H) is prepared by heating the cyano derivative of PPA with sodium azide and ammonium chloride at 80° C. in dimethylformamide for 24 hours (D. Carini et al., J. Med. Chem. 34:2525–47 (1991)).

The bisphosphonate (B) derivative of PPA (FIG. 1; 4, where $R_2$=H) is prepared by heating PPA with phosphorous acid and phosphorus trichloride, followed by hydrolysis of the resulting bisphosphonate dimer with 6 N hydrochloric acid (M. Francis et al., J. Chem. Educ 55: 760–766 (1978)).

The ethylenic precursor of HPPA benzyl ether is subjected to these same two reactions. The resulting tetrazole and bisphosphonate intermediates can be hydrogenated/debenzylated to afford monophenols T and B (3 and 4, respectively, where $R_2$=—OH) by stirring methanolic solutions of these with 5% palladium on powdered charcoal under three atmospheres of hydrogen gas (P. Ruenitz et al., J. Med. Chem. 39:4853–4859 (1996)).

Reaction progress and purity of final products can be monitored by high performance liquid chromatography (HPLC) using a 4.6×250 mm Econosil 5 μm 1-(n-octyl) silane column (Alltech, Inc., Deerfield Ill.) and a mobile phase (flow rate 1 mL/min) composed of methanol—200 mM diethylamine phosphate buffer pH 6.8 (70–30 v/v), with effluent monitoring at an ultraviolet wavelength of 254 nm. Mobile phase composition can be modified if necessary to optimize selectivity between each phenolic derivative and its nonphenolic counterpart, for application in the in vitro biotransformation studies described below.

Final compounds can be purified by crystallization as the free acids, or more likely as sodium, potassium, or tromethamine salts, then subjected to spectral characterization by proton nuclear magnetic resonance and electron impact mass spectrometry. Elemental composition can be determined by combustion analysis. All final compounds are expected to be racemic mixtures due to chirality of their diarylmethine carbons.

Example III

Characterization of HPPA in OVX Rats

The bone protective and uterine effects in OVX rats of 4HTA, a metabolite of tamoxifen (TAM) and HPPA, the dihydrodesethyl derivative of 4HTA previously characterized as a full estrogen mimetic in vitro (P. Ruenitz et al., J. Med. Chem. 39: 4853–4859 (1996)) were examined.

Materials and Methods

Chemicals

4HTA {4-[1-(p-hydroxyphenyl)-2-phenyl-1-butenyl]phenoxyacetic acid}, and HPPA {4-[1-(p-hydroxyphenyl)-2-phenylethyl]phenoxyacetic acid} were prepared and characterized as previously described (P. Ruenitz et al., J. Med. Chem. 39:4853–4859; 1996)). Briefly, 4HTA was produced from TAM by stepwise replacement of its dimethylaminoethyl side chain with an acetic acid moiety, accompanied by p-hydroxylation. HPPA was synthesized as described in Example I. All other chemicals were purchased from Sigma Chemical Co., St. Louis, Mo.

Animals and Dosing

In the first experiment 50 female Sprague-Dawley rats that were approximately 90 days of age and weighed an average of 240 g at the beginning of the study were used. Animal care and handling was carried out solely at the AAALAC accredited animal facility at the University of Georgia College of Pharmacy, in accordance with a protocol approved by the University of Georgia Institutional Animal Care and Use Committee. On the day of surgery (day 0), all rats were anesthetized with an intraperitoneal (i.p.) injection of ketamine hydrochloride and xylazine at doses of 50 mg/kg body weight and 10 mg/kg body weight, respectively. Ten rats were sham-operated during which the ovaries were exteriorized but replaced intact. Bilateral ovariectomies were performed in the remaining 40 rats from a dorsal approach. Each rat was housed individually at 25° C. with a light/dark cycle of 13 hours/11 hours. Food (Teklad 22/5 Rodent Diet, Madison, Wis.), with calcium and phosphate contents of 0.95% and 0.67%, respectively, was available ad libitum to all animals.

Sham-operated rats (N=10) and one of the four groups of OVX rats (N=10) were injected subcutaneously (s.c.) with vehicle (5% benzyl alcohol in corn oil) 5 days per week for 5 weeks. The remaining 20 OVX rats (N=10 per group) were subjected to the same treatment regimen with 17β-estradiol or HPPA at doses of 10 μg/kg/day or 3.6 mg/kg/day, respectively, administered s.c. in 5% benzyl alcohol-corn oil vehicle. The above treatments were initiated on the first day after surgery. The dose level of 17β-estradiol was believed to be optimal based on earlier studies (T. Wronski et al., Endocrinology 123:681–686 (1988)). The dose level of HPPA approximated maximally the effective bone protective dose levels of TAM and CLO (M. Jimenez et al. Endocrinology 138:1794–1800 (1997); L. Moon et al., Endocrinology 129:1568–1574 (1991)). Each rat was injected s.c. with demeclocycline and calcein (Sigma Chemical Co., St. Louis, Mo.) at a dose of 15 mg/kg body weight on the 10th and 3rd days before sacrifice, respectively, to label sites of bone formation.

A second experiment, using 40 animals, was performed in exactly the same manner described above, in which effects of the s.c. administration of 3.7 mg/kg/day of 4HTA to one group of OVX animals was compared to the effects of vehicle or 17β-estradiol in three other groups (vehicle treated sham OVX, vehicle treated OVX, and 17β-estradiol-treated OVX rats).

Necropsy Procedures

All rats were sacrificed by exsanguination from the abdominal aorta under ketamine/xylazine anesthesia. Failure to detect ovarian tissue and observation of marked atrophy of the uterine horns confirmed the success of ovariectomy. The body weight of each animal was recorded, as was uterine wet weight. Blood samples were allowed to coagulate at room temperature (2 hours) in a Vacutainer tube. Serum was obtained by centrifugation for 10 minutes at 3000 rpm, and samples were stored at −80° C. until analyzed. The right tibia was removed at necropsy, dissected free of muscle, and cut in half cross-sectionally with a hand-held saw (Dremel Moto Tool, Racine, Wis.). The bone samples were then placed in 10% phosphatebuffered formalin for 24 hours for tissue fixation.

Cancellous Bone Histomorphometry

The proximal halves of the tibiae were dehydrated by immersion in ethanol, and embedded undecalcified in methyl methacrylate. Longitudinal sections (4- and 8-μm thick) were cut with AO Autocut/Jung 1150 or 2050 microtomes. The 4-μm thick sections were stained according to the Von Kossa method with a tetrachrome counterstain (Polysciences Inc., Warrington, Pa.). Bone measurements were performed in cancellous bone tissue of the proximal tibial metaphysis beginning at distances 1 mm distal to the growth plate-metaphyseal junction to exclude the primary spongiosa. In general, two sections of the proximal tibia, with a total of 40–50 mm of cancellous bone perimeter, were sampled in each animal with an appreciable amount of cancellous bone. Additional sections were sampled in osteopenic animals to approximate the cancellous bone perimeter sampled in animals with greater cancellous bone mass.

Bone measurements were performed with the Bioquant Bone Morphometry System (R&M Biometrics Corp., Nashville, Tenn.) as described in T. Wronski et al. (Calcif. Tissue Int. 53:210–216 (1993)). Cancellous bone volume as a percentage of bone tissue area and osteoblast and osteoclast surfaces as percentages of total cancellous perimeter were measured in 4-μm thick, stained sections.

Fluorochrome-based indices of bone formation were measured in unstained, 8-μm-thick sections of the proximal tibial metaphysis. The percentage of cancellous bone surface with a double fluorochrome label (mineralizing surface) and mineral apposition rate were measured with the Bioquant system. In addition, bone formation rate (tissue level, total surface referent) was calculated by multiplying mineralizing surface by mineral apposition rate (H. Frost, Bone histomorphometry: analysis of trabecular bone dynamics. In: Recker R. R., Ed. Bone Histomorphometry: Techniques and Interpretation. Boca Raton, Fla.: CRC Press; 1983; 109–132).

Cortical Bone Histomorphometry

The distal halves of the tibiae were dehydrated in 10 changes of 100% ethanol, defatted in 10 changes of acetone (at least 2 hours per change), and embedded undecalcified in a styrene monomer that polymerizes into a polyester resin (Tap Plastics, San Jose, Calif.). The tibial diaphysis 1–2 mm proximal to the tibiofibular junction was sawed into 100-μm-thick cross sections with an Isomet low speed saw (Buehler, Lake Bluff, Ill.).

Bone measurements were performed with the Bioquant Bone Morphometry System (R&M Biometrics Corp., Nashville, Tenn.). Cortical bone tissue area and bone marrow area were measured in one section per animal at a magnification of 20×. Cortical bone area was calculated by subtracting marrow area from cortical bone tissue area. Cortical width was measured from the periosteal to the endocortical surfaces at four equally spaced sites at the anterior (cranial), posterior (caudal), medial, and lateral aspects of each cross-section. The four measurements were averaged to obtain a mean cortical width for each animal.

Fluorochrome-based indices of bone formation were measured under UV illumination at magnifications of 100× and 200× for mineralizing surface and mineral apposition rate, respectively. The percentage of periosteal surface with a double fluorochrome label (mineralizing surface) and interlabel distances along the double labeled surfaces were measured with the Bioquant system. The mineral apposition rate (MAR) and bone formation rate, surface referent (BFR/BS), were calculated according to the following formulas: MAR=interlabel distance/time interval between labels (7 days) and BFR/BS=mineralizing surface×MAR.

Serum Rat Osteocalcin Radioimmunoassay (RIA)

Materials, as well as standard protocols for their use, were obtained from Biomedical Technologies, Inc., Stoughton Mass. Serum samples from each member of the different treatment groups were diluted 1:20. Duplicate aliquots (100 μL) of each diluted sample were incubated in an orbital shaker at 80 rpm (4° C.) for 16 hours with the first antibody and nonimmune serum in RIA buffer (final volume 0.5 mL). An aliquot of [$^{125}$I]-osteocalcin (10 nCi, 0.034 ng) in 100 μL of RIA buffer was then added to each tube and incubation was continued for 24 hours. Then the second (precipitating) antibody was added in 1 mL of modified buffer, and incubation was continued for 4 hours. Tubes were then centrifuged at 1500×g for 15 minutes. Pellets were washed with cold distilled water and recentrifuged as before. Supernatant was decanted and radioactivity in pellets was determined using a gamma counter. Serum osteocalcin levels were determined by comparing the sample values (cpm) to the linear region of a standard curve of cpm/pellet vs. the amount of osteocalcin present, obtained from incubations to which known amounts (0–0.35 ng) of osteocalcin had been added. All values were corrected for nonspecific binding in standard incubations. Mean values (and SD) for treatment groups in each experiment are expressed relative to those of respective OVX-17β-estradiol treated groups.

Statistical Analysis

Data are expressed as the mean±SD for each group. Statistical differences among groups were evaluated by one-way Anova followed by the Fisher protected least significant difference (PLSD) test for multiple comparisons. Differences were considered significant at p<0.05.

Results

Results are shown in Table 2. With respect to sham-operated controls, ovariectomy resulted in an average 18.5% increase in overall body weight over the five-week course of the two studies. This increase was not observed in OVX animals receiving subcutaneous 17β-estradiol, 4HTA, or HPPA five days per week.

The effects of ovariectomy and the various treatments on mineralizing surface were similar to those described above for osteoblast surface with the exception that OVX rats treated with 17β-estradiol had a significantly lower mineralizing surface than the vehicle-treated control rats.

Mineral apposition rate (MAR) was significantly increased in vehicle-treated OVX rats compared to vehicle-treated controls rats at 35 days postsurgery (1.7 vs. 1.1 μm/day, P<0.05). In contrast, MAR was maintained at the control level in OVX rats treated with 17β-estradiol. Treatment with HPPA had no effect on MAR in OVX rats.

TABLE 2

Effect of various treatment regimens on OVX rats.
Results from experiment 2 are in italics.

| Treatment group | Body Weight, g | Uterine Weight, mg | Relative Serum OC Level[a] | BV/TV (%) | BFR/BS × $10^{-2}$ $\mu m^3/\mu m^2/d$. | OcS/BS (%) | Serum Cholesterol (mg/dL) |
|---|---|---|---|---|---|---|---|
| | | | mean (SD) | | | | |
| Sham Vehicle | 323 (16) | 776 (101) | 108 (21) | 22.5 (4.6) | 10.3 (3.3) | 1.8 (0.4) | 65 (2.2) |
| | 304 (14) | 613 (38) | 127 (33) | | | | |
| OVX Vehicle | 379 (23)[c] | 99 (19)[c] | 175 (21)[c] | 7.1 (2.8)[c] | 48.4 (11.8)[c] | 3.5 (0.9)[c] | 83 (2.5)[c] |
| | 364 (25)[c] | 86 (13)[c] | 176 (29)[c] | | | | |
| OVX 17β-estradiol | 310 (24)[b] | 269 (48)[b,c] | 100 (33)[b] | 24.1 (6.1)[b] | 7.3 (1.2)[b] | 1.6 (0.4)[b] | 80 (3.5)[c] |
| | 303 (12)[b] | 225 (30)[b,c] | 100 (16)[b] | | | | |
| OVX HPPA | 342 (23)[b,c] | 112 (7)[c] | 145 (27)[b,c] | 13.0 (4.7)[b,c,d] | 32.1 (5.9)[b,c,d] | 2.5 (0.4)[b,c,d] | 72 (1.9)[b,c,d] |
| OVX 4HTA | 305 (12)[b,c] | 124 (12)[b,c] | 188 (42)[c] | | | | |

[a]The mean amount of OC in serum from 17β-estradiol-treated animals was 4.20 + 1.39 ng/mL (experiment 1), 2.08 + 0.33 ng/mL (experiment 2).
[b]Different from OVX Vehicle (p<0.05).
[c]Different from Sham Vehicle (p<0.05).
[d]Different from OVX 17β-estradiol (p<0.05).

17β-Estradiol treatment resulted in 167% greater uterine weight (average of both experiments), compared to vehicle-treated OVX animals (Table 2). This increase was not as great as has been observed in related studies, in which higher doses and/or more potent derivatives of 17β-estradiol were administered. Similar comparative uterine weights in animals receiving 4HTA were 25% higher than respective OVX vehicle controls. Notably, the uterine weight of OVX animals receiving HPPA did not differ appreciably from that of OVX animals receiving vehicle.

Figure 2A:
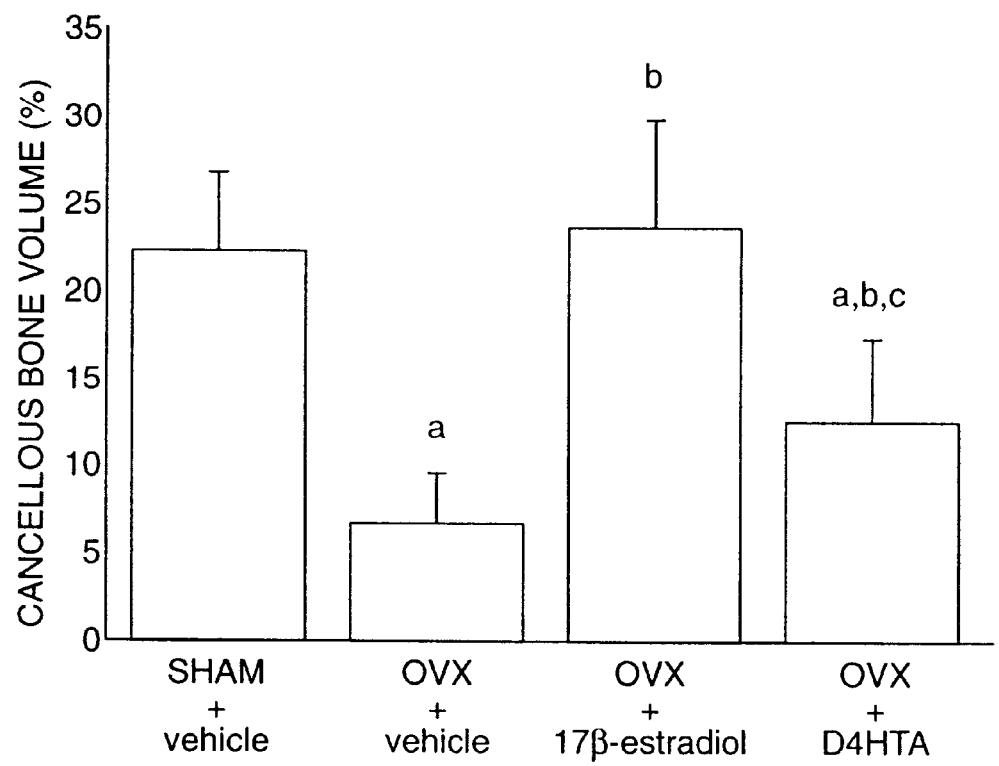
FIG. 2. Cancellous bone volume (A), osteoclast surface (B), osteoblast surface (C), and bone formation rate (D) in the proximal tibial metaphysis for the four groups of rats. Each bar is the mean ±SD for 10 animals; a, significantly different from vehicle-treated sham group (p<0.05); b, significantly different from vehicle-treated ovx group (p<0.05); c, significantly different from 17β-estradiol-treated ovx group (p<0.05).

Cancellous bone volume (BV/TV) was decreased by 68% in vehicle-treated OVX rats compared with vehicle-treated control rats (Table 2, FIG. 2A). In contrast, cancellous bone volume remained at the control level in OVX rats treated with 17β-estradiol, and treatment with HPPA partially prevented the OVX-induced cancellous bone loss. In the second experiment, cancellous bone volume in OVX rats treated with 4HTA (8.3±3.7%) did not differ from that of vehicle treated OVX animals (7.5±3.6%), but was lower than that of 17β-estradiol treated OVX animals (24.0±5.5%). This lack of effect on cancellous bone volume, and on serum OC levels (see below), precluded further detailed histomorphometric evaluation of 4HTA effects. Indices of bone turnover such as osteoclast surface (Oc.S/BS, Table 2, FIG. 2B) and osteoblast surface (FIG. 2C) of vehicle-treated OVX rats increased significantly compared to that of vehicle-treated control rats at 35 days after surgery. In contrast, these cellular indices of bone resorption and formation, respectively, were suppressed at the control level in OVX rats treated with 17β-estradiol. Treatment with HPPA partially suppressed the OVX-induced increase in osteoclast and osteoblast surfaces.

Cancellous bone formation rate (Table 2, BFR/BS, FIG. 2D) was significantly increased in vehicle-treated OVX rats when compared to vehicle-treated control rats. However, BFR/BS was suppressed at the control level in OVX rats treated with 17β-estradiol, whereas treatment with HPPA partially suppressed the OVX-induced increase in BFR/BS.

Figure 3:
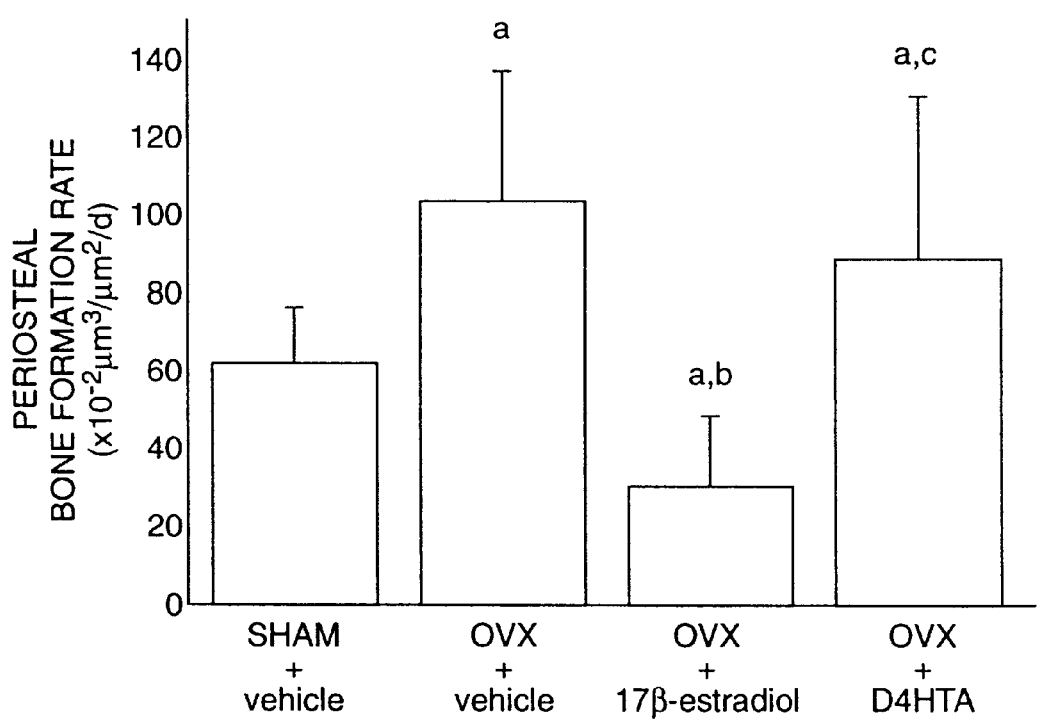
FIG. 3. Periosteal bone formation rate in the tibial diaphysis for the four groups of rats. Each bar is the mean ±SD for 10 animals; a, b, and c are as in FIG. 2.

Cortical bone area and marrow area did not differ significantly among groups as the mean values ranged from 5.2–5.4 mm$^2$ for the former variable and from 1.2–1.3 mm$^2$ for the latter variable. Mean values for cortical width were also similar at 0.8 to 0.9 mm for all 5 groups. However, periosteal bone formation rate (FIG. 3) was significantly increased in vehicle-treated OVX rats when compared with vehicle-treated control rats. 17β-estradiol treatment of OVX rats inhibited periosteal bone formation rate to a level below that of vehicle-treated control rats. Treatment of OVX rats with HPPA did not inhibit this skeletal process.

Ovariectomy resulted in an average 51% elevation of serum OC levels with respect to sham operated controls in the two experiments (Table 2). Administration of 17β-estradiol prevented this increase. OVX animals receiving HPPA exhibited a less pronounced (34%) increase in serum OC with respect to OVX vehicle controls, but serum OC levels in 4HTA-treated OVX animals did not differ from those in vehicle-treated OVX animals.

Administration of HPPA (10 μmol/kg sc) to OVX rats also resulted in a modest (10%) reduction in serum cholesterol with respect to vehicle-treated OVX animals (Table 2).

Discussion

4HTA

It is unlikely that 4HTA, a significant metabolite of TAM in the OVX rat (P. Ruenitz et al., Drug Metab. Dispos. 23:993–998 (1995)), contributes to the bone protective effect of its parent drug TAM. 4HTA exhibited effects on body weight and uterine weight suggestive of estrogenic activity, but it was ineffective in preventing loss of cancellous bone volume or elevation of serum osteocalcin after ovariectomy (Table 2).

HPPA

Figure 2B:
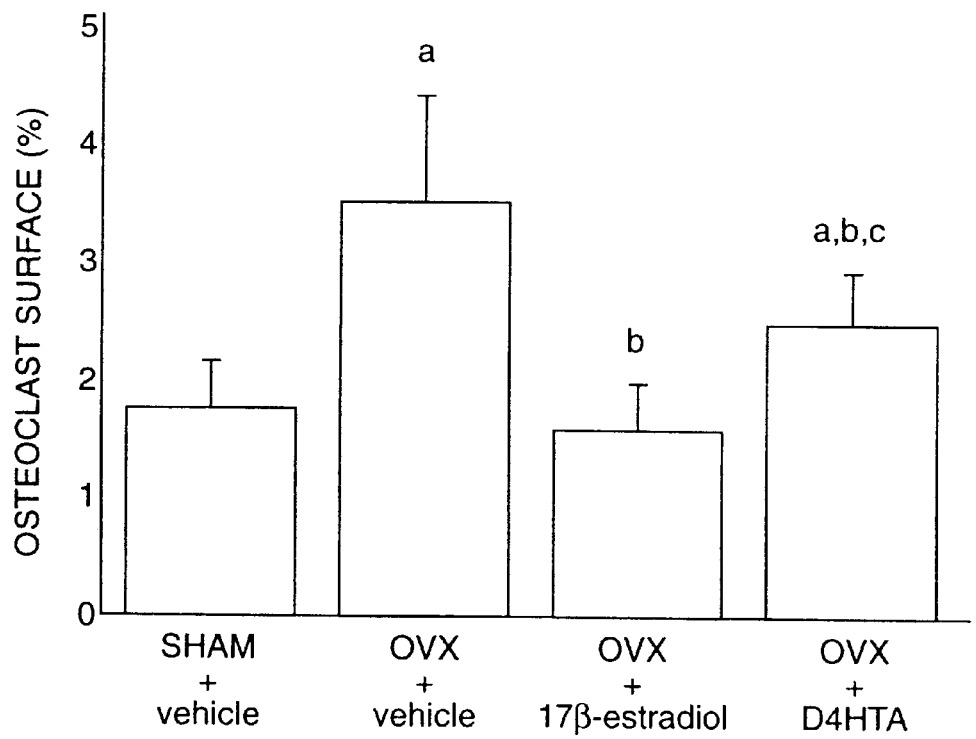
Figure 2C:
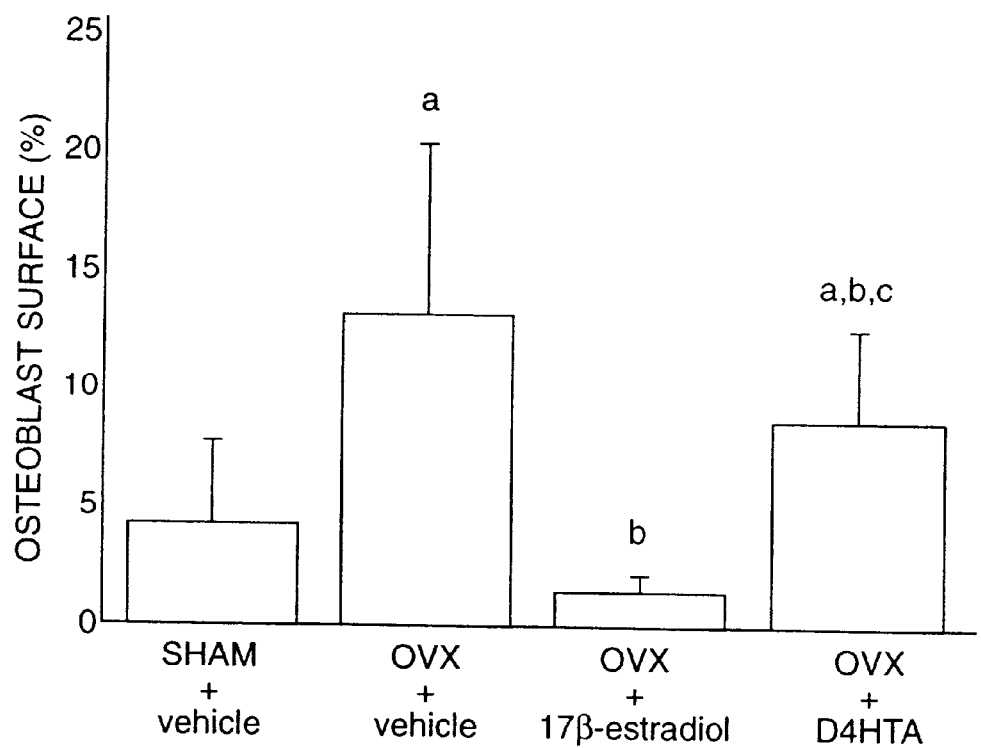
Figure 2D:
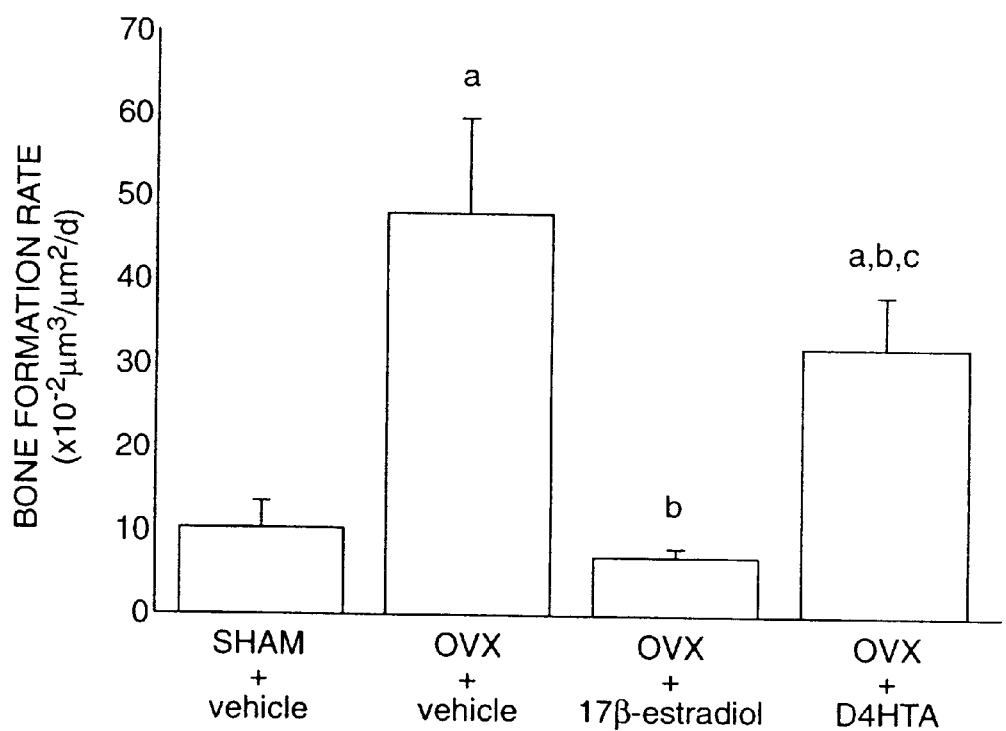

HPPA, a saturated analogue of 4HTA (FIG. 1), did not appreciably affect uterine weight loss associated with ovariectomy (Table 2), i.e., it was not uterotrophic, but it nevertheless partially prevented cancellous bone loss (FIG. 2A) and suppressed bone turnover indicators (FIGS. 2B,C, D, Table 2). Skeletal effects were less pronounced than those produced by a substantially lower dose level of 17β-estradiol, but were in general similar to those produced by equivalent dose levels of the parent compound TAM (C. Frolik et al., Bone 18:621–627 (1996); H. Ke et al., Bone 20:31–39 (1997); L. Moon et al., Endocrinology 129:1568–1574 (1991)).

Summary

Subcutaneous administration of HPPA (3.6 mg/kg) partially reduced bone turnover indicators and cancellous bone loss in a manner similar in many ways to that observed in TAM-treated OVX animals, but, surprisingly in view of its potent estrogenicity, had no uterotrophic effect. As such it is an excellent candidate for use in ERT. HPPA exhibits a bioactivity profile that was neither evident nor predictable from its chemical structure: relatively low ER affinity, full estrogenicity in the MCF-7 cell proliferation assay, not inhibitory of estrogen-stimulated cell proliferation, and significant estrogenic skeletal and cardiovascular effects in vivo; yet despite all these systemic effects characteristic of an estrogen mimetic, HPPA is substantially non-uterotrophic. This bioactivity profile is unique among candidate drugs for ERT. Other compounds which stimulate growth of estrogen responsive cells in vitro (e.g., in the MCF 7 cell proliferation assay) exhibit reproductive tract estrogenicity (Table 1; P. Ruenitz, Female sex hormones and analogs. In: Wolff, M. E., Ed. Burger's Medicinal Chemistry and Drug Discovery, Fifth Edition, vol 4. New York: John Wiley & Sons: 1997; 553–587), but HPPA, a full estrogen agonist in MCF-7 cells, did not appear to be uterotrophic in the animal model.

The complete disclosures of all cited patents, patent applications, publications and other documents are incorporated by reference as if fully set forth herein. The foregoing detailed description and examples have been given for clarity of understanding only. No unnecessary limitations are to be understood therefrom. The invention is not limited to the exact details shown and described, for variations obvious to one skilled in the art will be included within the invention defined by the claim.

What is claimed is:

1. A method for treating extra-reproductive tract tissues that are responsive to treatment with estrogen comprising administering to a patient an effective amount of a compound having the structure

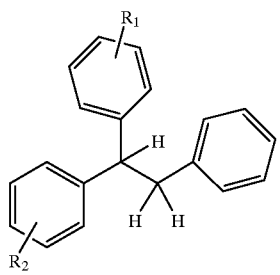

(I)

wherein $R_1$ is —O(CH$_2$)$_m$R$_3$ or —(CH$_2$)$_n$R$_3$; $R_3$ is an anionic substituent; m is 1, 2, 3 or 4; n is 0, 1, 2, 3 or 4; $R_2$ is H or meta-OH.

2. The method of claim 1 wherein $R_1$ is —O(CH$_2$)$_m$R$_3$.
3. The method of claim 1 wherein $R_1$ is —(CH$_2$)$_n$R$_3$.
4. The method of claim 1 wherein $R_2$ is meta-OH.
5. The method of claim 1 wherein $R_2$ is H.
6. The method of claim 5 wherein the compound is 4-(1-phenyl-2-phenylethyl)phenoxyacetic acid such that $R_1$ is —OCH$_2$R$_3$; $R_3$ is —COO$^-$; and each of $R_1$ and $R_2$ is para to its respective phenyl ethyl linkage.
7. The method of claim 1 wherein the anionic substituent comprises a functional group selected from the group consisting of a carboxylate group, a tetrazolate group and a bisphosphonate group.
8. The method of claim 1 wherein the patient is a female.
9. The method of claim 8 wherein the patient is a perimenopausal or postmenopausal female.
10. The method of claim 1 wherein the compound is administered in an estrogen replacement therapy.
11. The method of claim 1 wherein the compound is administered to treat osteopenia.
12. A compound having the structure

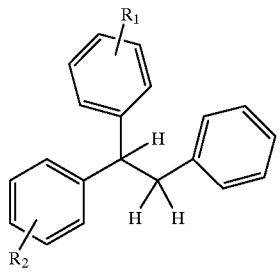

(I)

wherein $R_1$ is —O(CH$_2$)$_m$R$_3$ or —(CH$_2$)$_n$R$_3$; $R_3$ is an anionic substituent; m is 1, 2, 3 or 4; n is 0, 1, 2, 3 or 4; $R_2$ is H or meta-OH.

13. The compound of claim 12 wherein $R_1$ is —O(CH$_2$)$_m$R$_3$.
14. The compound of claim 12 wherein $R_1$ is —(CH$_2$)$_n$R$_3$.
15. The compound of claim 12 wherein $R_2$ is meta-OH.
16. The compound of claim 12 wherein $R_2$ is H.
17. The compound of claim 16 which is 4-(1-phenyl-2-phenylethyl)phenoxyacetic acid such that $R_1$ is —OCH$_2$R$_3$; $R_3$ is —COO$^-$; and each of $R_1$ and $R_2$ is para to its respective phenyl ethyl linkage.
18. The compound of claim 12 wherein the anionic substituent comprises at least one functional group selected from the group consisting of a carboxylate group, a tetrazolate group and a bisphosphonate group.
19. A pharmaceutical composition comprising a compound having the structure

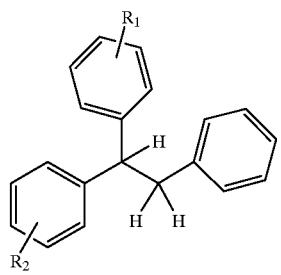

(I)

wherein $R_1$ is —O(CH$_2$)$_m$R$_3$ or —(CH$_2$)$_n$R$_3$; $R_3$ is an anionic substituent; m is 1, 2, 3 or 4; n is 0, 1, 2, 3 or 4; $R_2$ is H or meta-OH; or a pharmaceutically acceptable salt thereof; and a pharmaceutically acceptable carrier.

20. The pharmaceutical composition of claim 19 wherein $R_1$ is —O(CH$_2$)$_m$R$_3$.

21. The pharmaceutical composition of claim 19 wherein $R_1$ is —(CH$_2$)$_n$R$_3$.

22. The pharmaceutical composition of claim 19 wherein $R_2$ is meta-OH.

23. The pharmaceutical composition of claim 19 wherein $R_2$ is H.

24. The pharmaceutical composition of claim 23 wherein the compound is 4-(1-phenyl-2-phenylethyl)phenoxyacetic acid such that $R_1$ is —OCH$_2$R$_3$; $R_3$ is —COO$^-$; and each of $R_1$ and $R_2$ is para to its respective phenyl ethyl linkage.

* * * * *